United States Patent [19]

Dexter et al.

[11] 4,233,209
[45] Nov. 11, 1980

[54] HINDERED PHENOL HYDRAZONES AND COMPOSITIONS STABILIZED THEREWITH

[75] Inventors: Martin Dexter, Briarcliff Manor; David H. Steinberg, Bronx, both of N.Y.

[73] Assignee: Ciba-Geigy Corporation, Ardsley, N.Y.

[21] Appl. No.: 960,979

[22] Filed: Nov. 15, 1978

Related U.S. Application Data

[63] Continuation of Ser. No. 839,683, Oct. 5, 1978, abandoned, which is a continuation-in-part of Ser. No. 756,030, Dec. 30, 1976, abandoned.

[51] Int. Cl.$^3$ .................. C08K 5/36; C07C 103/30; C08K 5/30; C07C 103/58
[52] U.S. Cl. .................. 260/45.85 E; 260/45.85 R; 260/45.9 NC; 260/404.5; 560/221; 560/251; 564/150
[58] Field of Search .................. 260/559 H, 45.9 NC, 260/45.8 E, 404.5, 45.85 R; 560/221, 254, 251

[56] References Cited

U.S. PATENT DOCUMENTS

| | | | |
|---|---|---|---|
| T857,036 | 12/1968 | Straley et al. | 260/559 H |
| 3,547,646 | 12/1970 | Hori et al. | 260/559 H |
| 3,549,572 | 12/1970 | Minagawa et al. | 260/559 H |
| 3,745,163 | 7/1973 | Holt et al. | 260/559 H |
| 3,773,830 | 11/1973 | Dexter | 260/559 H |
| 3,894,083 | 7/1975 | Hofer et al. | 260/559 H |
| 4,073,771 | 2/1978 | Hartless et al. | 260/559 H |

FOREIGN PATENT DOCUMENTS

2711207 9/1978 Fed. Rep. of Germany .
41-1940 2/1966 Japan .
49-1501 1/1974 Japan .
566836 7/1977 U.S.S.R. .

*Primary Examiner*—V. P. Hoke
*Attorney, Agent, or Firm*—Luther A. R. Hall

[57] ABSTRACT

Hindered phenol hydrazones of the formula

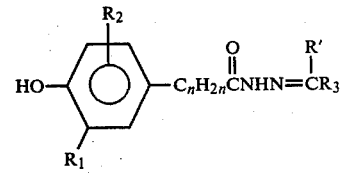

wherein $R_1$ and $R_2$ are alkyl of 1 to 8 carbons or $R_1$ can also be hydrogen, n is 1 to 6, R' is hydrogen or alkyl, $R_3$ is alkyl, phenyl, substituted phenyl, alkylenethioalkyl or alkylenethioether ester of a carboxylic acid or a group

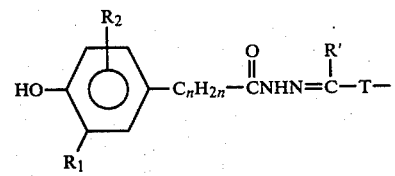

where T is a direct bond, alkylene, sulfur or oxygen interrupted alkylene or phenylene, said compounds being useful as diene rubber stabilizers.

16 Claims, No Drawings

HINDERED PHENOL HYDRAZONES AND COMPOSITIONS STABILIZED THEREWITH

This is a continuation of application Ser. No. 839,683, filed on Oct. 5, 1977, now abandoned, which in turn is a continuation-in-part of application Ser. No. 756,030, filed on Dec. 30, 1976, now abandoned.

The present invention is directed to a novel class of hindered phenol hydrazone compounds which are useful as stabilizers for polymers. These hydrazones are of the formula

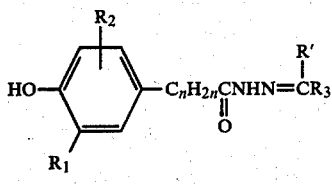

wherein
$R_1$ is hydrogen or a straight or branched chain alkyl of 1 to 8 carbon atoms,
$R_2$ a straight or branched chain alkyl of 1 to 8 carbon atoms,
n is an integer of 1 to 5, preferably 2, and
$R'$ is hydrogen or alkyl of 1 to 8 carbon atoms,
$R_3$ is an alkyl of 1 to 18 carbon atoms, phenyl or phenyl substituted with 1 to 3 alkyl groups of 1 to 4 carbon atoms, an interrupted alkyl selected from the formulae

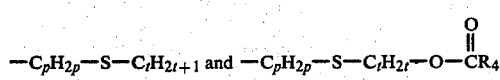

where p and t are independently integers of 1 to 18, $R_4$ is an alkyl group of 1 to 17 carbon atoms or an olefinic group of the formula $-(CH_2)_z-CH=CH(CH_2)_y CH_3$ where z and y are independently integers of 1 to 12, or $R_3$ is the group

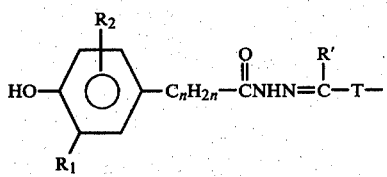

where T is a direct bond, alkylene of 1 to 6 carbon atoms, phenylene alkylene interrupted with sulfur or oxygen of the formula $-(C_aH_{2a})-X-(C_aH_{2a})-$ where X is sulfur or oxygen and a is an integer of 1 to 6.

$R_1$, $R_2$, and $R'$ as alkyl are, for example, independently of one another, straight-chain or branched alkyl with 1-8 carbon atoms, such as methyl, ethyl, n-propyl, iso-propyl, n-butyl, sec.-butyl, tert.-butyl, 2-ethylbutyl and n-octyl and tert-octyl. For $R_1$ and $R_2$ α-branched alkyl radicals with 3–8 carbon atoms are preferred and tert-butyl is especially preferred. The group $R^1$ is preferably hydrogen or an alkyl of 1 to 4 carbons.

In the definition of $R_3$ preferred are alkyl which can be straight or branched chain, or phenyl, and when it is an interrupted alkyl preferably integer p is 2 to 6, and especially 2 to 4 and t is 8 to 18. The integers z and y are preferably 4 to 12. When $R_3$ is a hindered phenolic alkanoate hydrazone group of the above formula, T is preferably a direct bond, alkylene of 1 to 4 carbons or various isomers of phenylene such as 1,3- 1,4 or 1,2-phenylene. When T is an interrupted alkylene, X is preferably sulfur and a is 1 or 2, especially 1.

The novel hindered phenol hydrazone compounds of this invention are prepared by a procedure involving the reaction of a hindered phenol hydrazine with an alkyl or substituted alkyl aldehyde or a ketone where the substituent is a thioalkyl or a thioalkylene ester group. The hindered phenol hydrazines and their preparation are disclosed in U.S. Pat. No. 3,660,438 which are incorporated herein by reference. The classes of aldehydes and the ketones, employed in the preparation of the hydrazones are known and may be illustrated by the following formulas:

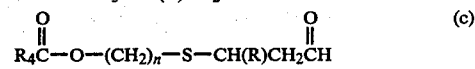

where $R_4$ is as defined above and $R_5$ is alkyl of 1–12 carbons or aryl, especially phenyl and alkyl substituted phenyl and R is methyl or hydrogen. The reaction is generally carried out in a non-reactive solvent such as an alcohol at a temperature of 25° to 100° C. and preferably 40°–70° C. for about 2 to 5 hours. It is sometimes advantageous to use a catalytic amount of a Lewis Acid such as $AlCl_3$, $MgBr_2$ or $ZnCl_2$ and especially $BF_3$, or even acids such as hydrochloric, sulfuric or phosphoric, to hasten the reaction. This is especially applicable when less reactive ketones are used as one of the reactants. Aldehydes (a) are generally commercially available and also can be prepared by oxidation of the corresponding alcohols, reduction of the corresponding acids or by rearrangement of the terminal epoxides. Aldehydes (b) can be most conveniently prepared by the base catalyzed addition of a mercaptan to an α,β-unsaturated aldehyde. Aldehydes (c) can be prepared by the same method as aldehydes (b) except for the use of mercaptans of the formula

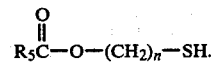

Ketones (d) are generally commercially available or could be prepared by the oxidation of the corresponding secondary alcohols or by condensation of two molecules of the same or different acids in the presence of base.

The compounds of this invention are useful as stabilizers of various polymers, especially olefin homopolymers and copolymers are diene rubbers. Illustrative examples of olefin polymers are:

1. Polymers which are derived from mono- or diolefines, for example polyethylene which can optionally be crosslinked, polypropylene, polyisobutylene, polymethylbutene-1, polymethylpentene-1, polyisoprene, polybutadiene.

2. Mixtures of the homopolymers listed under (1), for example mixtures of polypropylene and polyethylene, polypropylene and polybutene-1, polypropylene and polyisobutylene.

3. Copolymers of the monomers based on the homopolymers listed under (1), for example ethylene/propylene copolymers, propylene/butene-1 copolymers, propylene/isobutylene copolymers, ethylene-butene-1 copolymers as well as terpolymers of ethylene and propylene with a diene, for example hexadiene, dicyclopentadiene or ethylidene norbornene, or monoolefins copolymerized with acrylates, methacrylates, vinyl acetate or similar comonomers.

The substrates that the compounds of this invention stabilize particularly well are diene containing rubbers such as polybutadiene and butadiene copolymers such as SBR (styrene-butadiene rubber), ABS (acrylonitrile-butadiene-styrene copolymer, thermoplastic SBR (styrene-butadiene-styrene block copolymers), methacrylateacrylonitrile-butadiene-styrene copolymers and barrier resins (high acrylonitrile ABS copolymers) as well as various ethylene-propylene-diene rubbers. The above stabilizers are employed in amounts of from 0.01 to 5% by weight of the butadiene rubber. More preferably, the concentratiion of the stabilizer is from 0.05 to 2% by weight of the rubber. It is envisioned that prior to and/or during manufacturing, additional stabilizers and other additives may be added.

The following examples are presented below for the purpose of illustration of the present invention and not to be considered as limiting the invention.

EXAMPLE 1

Preparation of 3-(3″,5″-di-t-butyl-4′-hydroxyphenyl) propionyl hydrazide

Methyl 3-(3′,5′-di-t-butyl-4′-hydroxyphenyl)propionate (146 g, 0.5 moles) is dissolved in 500 ml of dry methanol. To this solution is added at room temperature hydrazine hydrate (101 g, 2 moles). The mixture is then refluxed for 10 hours. Upon cooling to room temperature the product crystallizes out. It is harvested by filtration, washed with some cold methanol and dried. There is obtained 116.7 g (80% yield) of white solid having melting point 149°–151° C.

EXAMPLE 2

Preparation of n-dodecylthio-3-methylpropanal

To a stirred solution of n-dodecyl mercaptan (202 g, 1.0 moles) and triethylamine (2 g) was added crotonaldehyde (72 g, 1.0 mole) over 65 minutes while maintaining a temperature of 55°–60° C. After complete addition the resulting reaction mixture was heated at 85° C. for 0.5 hour. Thin layer analysis (TLC) showed the reaction to be complete and this intermediate was used to prepare the product described in Example 3 without further purification.

If in the above reaction acrolein or cinnamaldehyde are used in place of crotonaldehyde, n-dodecylthiopropanal and n-dodecylthio-3-phenylpropanal respectively are obtained.

EXAMPLE 3

Preparation of n-dodecylthio-2-methylpropanal-3-(3′,5′-di-t-butyl-4′-hydroxyphenyl)propionyl hydrazone A stirred mixture of 3-(3′,5′-di-t-butyl-4′-hydroxyphenyl) propionyl hydrazide (58.4 g, 0.20 moles) prepared in Example 1 in 2-propanol (500 ml) was heated to 60° C. To this was added dropwise over 15 minutes n-dodecylthio-3-methyl-propanal (54.5 g, 0.20 moles) prepared in Example 2. The resulting solution was stirred at reflux for 3.5 hours. The solvent was then stripped at 70° C./20 mm. There was obtained 112 g. of residue which solidified to a white solid having melting point 53°–7° C. The crude product was recrystallized from a mixture of ethanol (750 ml) and water (50 ml) and afforded 82 g. of solid having M.P. 69°–72° C. which gave the following analysis.

Calc'd for $C_{33}H_{57}N_2O_2S$: C, 72.61; H, 10.52; N, 5.13; S, 5.87. Found: C, 72.76; H, 10.97; N, 5.22; S, 5.78.

EXAMPLE 4

Preparation of n-dodecylthiopropanal-3-(3′,5′-t-butyl-4′-hydroxyphenyl) propionyl hydrazone When the procedure of Example 3 is followed except that n-dodecylthiopropanal (prepared in the second part of Example 2) is employed, the above named compound is obtained.

EXAMPLE 5

Preparation of ethylthio-3-methylpropanaloleate-3′-(3″,5″-di-t-butyl-4″-hydroxyphenyl)propionyl hydrazone A solution of 3-(3′,5′-di-t-butyl-4′-hydroxyphenyl)-propionyl hydrazide (13.89 g, 0.0475 moles) in 125 ml of 2-propanol was heated to 60° C. while stirring under nitrogen. To this was added a solution of ethylthio-3-methylpropanal oleate over about 0.25 hour. Following addition the resulting mixture was stirred and heated at reflux for 4 hours. After cooling the reaction mixture was stripped of solvent and dried to afford an amber syrup. NMR analysis confirmed the formation of the desired product which gave the following analysis:

Calc'd for $C_{41}H_{70}O_4N_2S$: C, 71.67; H, 10.27; N, 4.08. Found: C, 71.89; H, 9.80; N, 4.74.

In a like manner one may employ ethylthio-3-methylpropanal oleate, ethylthio-3-methylpropanal stearate, ethylthio-3-methylpropanal laurate or ethylthio-3-methylpropanal acetate to yield the corresponding products.

EXAMPLE 6

Following the procedure of Example 3 and employing the appropriate reactants, the following compounds were prepared:
(a) n-Tridecylthio-3-methylpropanal-3′-(3″,5″-di-t-butyl-4″-hydroxyphenyl)propionyl hydrazone—a syrup
(b) n-Dodecylal-3-(3′,5′-di-t-butyl-4′-hydroxyphenyl)-propionyl hydrazone—m.p. 74°–77° C.
(c) N-2-Octylidene-N′-3′-(3″,5″-di-t-butyl-4″-hydroxyphenyl) propionyl hydrazone—83°–88° C.
(d) N-α-Methylbenzylidine-N′-3′-(3,″5″-di-t-butyl-4″-hydroxyphenyl)propionyl hydrazone—192°–196° C.
(e) N-2,6,8-Trimethyl-4-nonylidene-N′-3′-(3″,5″-di-t-butyl-4″-hydroxyphenyl)propionyl hydrazone—a syrup
(f) 2,3-Dimethylvaleral-3′-(3″,5″-di-t-butyl-4″-hydroxyphenyl) propionyl hydrazone—m.p. 109°–113° C.
(g) Isovaleral-3-(3′,5′-di-t-butyl-4-hydroxyphenyl)propionyl hydrazone—m.p. 177°–180° C.

(h) 5-Methyl-2-pentylidene-3'-(3",5"-di-t-butyl-4-hydroxyphenyl) propionyl hydrazone—m.p. 149°–152° C.

(i) 2-Methylpropylal-3'-(3",5"-di-t-butyl-4"-hydroxyphenyl) propionyl hydrazone—m.p. 195°–198° C.

(j) n-Pentylal-3-(3',5'-di-t-butyl-4-hydroxyphenyl)propionyl hydrazone—m.p. 149°–151° C.

(k) 1,4-Phenylene diformal bis{3'-(3",5"-di-t-butyl-4-hydroxyphenyl)propionyl hydrazone)}—m.p. 275°–280° C. d.

(l) Ethanedial bis {3-(3',5'-di-t-butyl-4-hydroxyphenyl) propionyl hydrazone}—m.p. 271°–273° C.

(m) 1,3-Propanedial bis {3'-(3",5"-di-t-butyl-4"-hydroxyphenyl) propionyl hydrazone}—m.p. 150°–157° C.

(n) 1,3-Phenylene diformal bis {3'-(3",5"-di-t-butyl-4-hydroxyphenyl)propionyl hydrazone}—m.p. 253°–261° C.

Also following the procedure of Example 3 except that appropriate starting materials are employed, the following compounds are prepared:

n-Dodecylthio-3-methylpropanal-3'-(3",5"-di-t-octyl-4"-hydroxyphenyl)propionyl hydrazone n-Octadecylthio-octadecanal 2-(3'-5'-dimethyl-4'-hydroxyphenyl) acetyl hydrazone n-Octylthioethanal 3-(3'-methyl-5'-t-butyl-4'-hydroxyphenyl) propionyl hydrazone n-Dodecylthiopropanal 3-(3'-6'-di-t-butyl-4'-hydroxyphenyl) propionyl hydrazone

EXAMPLE 7

Preparation of N-1,7-Dimethyl-4-heptylidene N'-3'-(3",5"-di-t-butyl-4"-hydroxyphenyl)propionyl hydrazone A mixture consisting of 3-(3',5'-di-t-butyl-4'-hydroxyphenyl)propionyl hydrazide (14.62 g, 0.05 moles), prepared as described in Example 1, di-isobutyl ketone (7.82 g, 0.055 moles) 2nd 2-propanol (100 ml) was stirred and heated at reflux for 5 hours. A catalytic quantity (0.5 ml) of boron trifluoride etherate (47% w/v) was added and refluxing continued for an additional 1.5 hours. After cooling to room temperature and distillation of the solvent under reduced pressure, and residue consisting of 20.6 g. of white solid was obtained. Two recrystallization from heptane afforded 13.2 g. of the product having m.p. 132°–9° C. After drying for 5 hours at 100°/0.1 mn, the following analysis was obtained.

Calc.d for $C_{26}H_{44}N_2O_2$: C, 74.95; H, 10.65; N, 6.72. Found: C, 75.17; H, 11.07; N, 6.61.

Following the procedure of Example 7, except for employing appropriate starting materials, the following compounds were prepared:

(a) 5-Methyl-3-heptylidene-3'-(3",5"-di-t-butyl-4"-hydroxyphenyl)propionyl hydrazone—m.p. 114°–120° C.

(b) 4-Methyl-2-octylidene-3'-(3",5"-di-t-butyl-4"-hydroxyphenyl)propionyl hydrazone—a yellow syrup (c) N-α-n-Butylbenzylidene-N'-3-(3',5'-di-t-butyl-4'-hydroxyphenyl)propionyl hydrazone—m.p. 161°–163° C.

The above described hindered phenol hydrazone compounds, as already stated above, are useful as butadiene containing rubber stabilizers. Additionally these compounds can also be used as stabilizers of natural and synthetic oils, especially as stabilizers of turbine oils. The examples below further illustrate the present invention, especially dealing with the compositions stabilized with the hydrazone compounds described above.

Extraction of Stabilizer from Commercial Rubber

The rubber substrates employed in the below described tests were commercially available materials which contain BHT commercial stabilizer. Therefore before such rubbers can be used for testing, it is first necessary to extract BHT from the substrate. This is accomplished by dissolving the rubber (polybutadiene or polyisoprene) in toluene and precipitating it with isopropanol. This is repeated twice after which the rubber is dried to constant weight under vacuum at room temperature.

Stabilization of Polybutadiene During Processing

Dried polybutadiene (Solprene 235) from which commercial stabilizer BHT has been removed and the desired amount of the hydrazone stabilizer of this invention is quickly charged into a Brabender Plasticorder mixer and blended. While the blades are rotating the chart starts recording the torque. The mixing is continued at 60 rpm and 150° C. for 30 min. or until the sample crosslinks. As the mixing proceeds the torque usually decreases gradually until the onset of crosslinking. When torque is plotted against time the slope of the curve at first will be negative but at the onset of crosslinking it will be positive. Thus the inflection in the curve is recorded as the time when crosslinking occurs.

TABLE I

| Stabilizer | Time to Crosslinking |
|---|---|
| Bank | 1 min. |
| 0.1% Compd Ex. 3 | 10 min. |
| 0.2% Compd Ex. 3 | 15 min. |
| 0.1% Compd Ex. 5 | 8 min. |
| 0.1% Compd Ex. 6 | 5 min. |
| 0.2% Compd Ex. 6 | 19 min. |
| Blank | 8 min. |
| 0.2% Compd Ex. 6(b) | 19 min. |
| 0.2% Compd Ex. 6(a) | 9 min. |
| 0.2% Compd Ex. 6(j) | 15 min. |
| Blank | |
| 0.2% Compd Ex. 6(c) | 26 min. |
| 0.2% Compd Ex. 6(d) | 30 min. |
| 0.2% Compd Ex. 6(e) | 25 min. |
| 0.2% Compd Ex. 6(f) | 25 min. |
| 0.2% Compd Ex. 7 | 25 min. |
| 0.2% Compd Ex. 6(g) | 30 min. |

NOTE:
The horizontal lines in the above Table separate different testing series carried out at different times.

Polybutadiene Oven Aging at 70° C.

The desired amount of the stabilizer is incorporated into polybutadiene (Solprene 235, the commercial stabilizer having been extracted) with a Brabender Plasticorder at 110° C. using nitrogen atmosphere. After one minute of mastication the stabilizer is added and the rubber is mixed for additional four minutes. 70 mil 1 in. × 1 in. (2.54 cm × 2.54 cm) plaques were compression molded from the mixed rubber. The plaques were then oven aged at 70° C. to determine the onset of gellation. Polybutadiene is normally soft so that it can be easily cut with a spatula or a finger nail. With crosslinking it hardens and eventually becomes brittle. The onset of gellation occurs when the sample cannot be easily cut with spatula or a finger nail. With crosslinking it hardens and eventually becomes brittle. The onset of gellation occurs when the sample cannot be easily cut with spatula or a finger nail but actually recovers its original shape after the spatula is removed. In the table below are the oven aging test results.

TABLE II

| Stabilizer | Onset of Gel. |
| --- | --- |
| Blank | 65 hrs. |
| 0.1% Compd Ex. 3 | 1014 hrs. |
| 0.1% Compd Ex. 5 | 590 hrs. |
| 0.2% Compd Ex. 6(b) | 672 hrs. |
| 0.2% Compd Ex. 6(j) | 384 hrs. |

NOTE:
The horizontal lines in the above Table separate different testing series carried out at different times.

Polyisoprene Oven Aging at 100° C.

A stabilizer at the indicated concentration level is incorporated into rubber in a Brabender Plasticorder at 110° C. for four minutes under a nitrogen atmosphere. Twenty-five mil thick compression molded plaques, $2'' \times 1'' \times 0.025''$ (5.08 cm $\times$ 2.54 cm $\times$ 0.635 mm) weighing about 1 gm., are oven aged at 100° C. in a forced draft oven.

The sample becomes sticky and soft with the onset of decomposition. The sample is considered to have failed at the first indication of stickiness.

The hindered phenol hydrazone compounds of this invention may be employed in combination with other known additives, such as antiozonants, UV-light stabilizers and light absorbers, metal deactivators, and others.

The following may be mentioned as examples of further additives with which the stabilisers can be conjointly employed.

1. Antioxidants 1.1. Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethyl-phenol and 2,6-dioctadecyl-4-methylphenol.

1.2. Derivatives of alkylated hydroquinones, such as, for example, 2,5-di-tert.-butyl-hydroquinone, 2,5-di-tert.-amyl-hydroquinone, 2,6-di-tert.-butyl-hydroquinone, 2,5-di-tert.-butyl-4-hydroxy-anisole, 3,5-di-tert.-butyl-4-hydroxy-anisole, tris-(3,5-di-tert.-butyl-4-hydroxyphenyl)-phosphite, 3,5-di-tert.-butyl-4-hydroxyphenyl-stearate and bis-(3,5-di-tert.-butyl-4-hydroxyphenyl)-adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.

1.4. Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-ditert.-butylphenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecyl-mercapto-butane, 1,1,5,5-tetra-(5-tert.butyl-4-hydroxy-2-methylphenyl)-pentane and ethylene glycol bis-[3,3-bis-(3'-tert.butyl-4'-hydroxyphenyl)-butyrate].

1.5. O-, N- and S-benzyl compounds, such as, for example, 3,5,3',5'-tetra-tert.butyl-4,4'-dihydroxydibenzyl ether, 4-hydroxy-3,5-dimethylbenzyl-mercaptoacetic acid octadecyl ester, tris-(3,5-di-tert.butyl-4-hydroxybenzyl)-amine and bis-(4-tert.butyl-3-hydroxy-2,6-dimethylbenzyl)-dithioterephthalate.

1.6. Hydroxybenzylated malonic esters, such as, for example, 2,2-bis-(3,5-tert.butyl-2-hydroxybenzyl)-malonic acid dioctadecyl ester, 2-(3-tert.butyl-4-hydroxy-5-methyl-benzyl)-malonic acid dioctadecyl ester, 2,2-bis-(3,5-di-tert.butyl-4-hydroxybenzyl)-malonic acid didodecylmercaptoethyl ester and 2,2-bis-(3,5-di-tert.butyl-4-hydroxybenzyl)-malonic acid and di-[4-(1,1,3,3-tetramethylbutyl)-phenyl]ester.

1.7. Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8. s-Triazine compounds, such as, for example, 2,4-bis-octylmercapto-6-(3,5-di-tert.butyl-4-hydroxyanilino)-s-triazine, 2-octylmercapto-4,6-bis-(3,5-di-tert.butyl-4-hydroxyanilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxy-phenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9. Amides of β-(3,5-di-tert.butyl-4-hydroxyphenyl)-propionic acid, such as, for example, 1,3,5-tris-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.10. Esters of β-(3,5-di-tert.butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, trishydroxyethyl isocyanurate and 4-hydroxymethyl-1-phospha-2,6,7-trioxabicyclo[2,2,2]-octane.

1.11. Esters of β-(5-tert.butyl-4-hydroxy-3-methylphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, trishydroxyethyl isocyanurate and 4-hydroxymethyl-1-phospha-2,6,7-trioxabicyclo-[2,2,2]-octane.

1.12. Esters of 3,5-di-tert.butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thio-diethylene glycol, neopentyl glycol, pentaerythritol, 3-thia-undecanol, 3-thia-pentadecanol, trimethylhexanediol, trimethylolethane, trimethylolpropane, trishydroxyethyl isocyanurate and 4-hydroxymethyl-1-phospha-2,6,7-trioxabicyclo-[2,2,2]-octane.

1.13. Benzylphosphonates, such as, for example, 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.14. Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.octyl-p-phenylenediamine, N,N'-di-(1,4-dimethylpentyl)-p-phenylenediamine, N,N'-dimethyl-N,N'-di-(sec.octyl)-p-phenylenediamine, 2,6-dimethyl-4-methoxyaniline, 4-ethoxy-N-sec.-butylaniline, the condensation product of diphenylamine and acetone, and phenothiazine.

2. UV absorbers and light stabilizers 2,1. 2-(2'-Hydroxyphenyl)-benztriazoles, such as, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.amyl-, 3'-methyl-5'-carbomethoxyethyl- and 5-chloro-3',5'-di-tert.-amyl-derivative.

2.2. 2,4-Bis-(2'-hydroxyphenyl)-6-alkyl-s-triazines, such as, for example, 6-ethyl-, 6-heptadecyl or 6-undecyl-derivative.

2.3. 2-Hydroxybenzophenones, such as, for example, the 4-hydroxy-, 4-methoxy-, 4-octoxy-, 4-decyloxy-, 4-dodecyloxy-, 4-benzyloxy, 4,2',4'-trihydroxy- or 2'-hydroxy-4,4'-dimethoxy-derivative.

2.4. 1,3-Bis-(2'-hydroxybenzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids, such as, for example, phenyl salicylate, octylphenyl salicylate, dibenzoylresorcinol, bis-(4-tert.-butylbenzoyl)-resorcinol, benzoylresorcinol and 3,5-di-tert.-butyl-4-hydroxybenzoic acid 2,4-di-tert.butyl-phenyl ester, octadecyl ester or 2-methyl-4,6-di-tert.butyl-phenyl ester.

2.6. Acrylates, such as, for example, α-cyano-β,β-diphenylacrylic acid ethyl ester or isooctyl ester, α-carbomethoxycinnamic acid methyl ester, α-cyano-β-methyl-p-methoxycinnamic acid methyl ester or butyl ester and N-(β-carbomethoxyvinyl)-2-methyl-indoline.

2.7. Nickel compounds, such as, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel complexes of bis-[2-hydroxy-4-(1,1,3,3-tetramethylbutyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert.butylbenzyl-phosphonic acid monoalkyl esters, such as of the methyl, ethyl or butyl ester, nickel complexes of ketoximes such as of 2-hydroxy-4-methyl-phenylundecylketonoxime, nickel 3,5-di-tert.butyl-4-hydroxybenzoate and nickel isopropylxanthate.

2.8. Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl)-sebacate and 3-n-octyl-7,7,9,9-tetramethyl-1,3,8-triaza-spiro[4,5]decane-2,4-dione.

2.9. Oxalic acid diamides, such as, for example, 4,4'-dioctyloxy-oxanilide, 2,2'-dioctyloxy-5,5'-di-tert.butyl-oxanilide, 2,2'-didodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyl-oxanilide and its mixture with 2-ethoxy-2'-ethyl-5,4'-di-tert.butyl-oxanilide and mixtures of ortho- and para-methoxy- as well as of o- and p-ethoxy-disubstituted oxanilides.

3. Metal deactivators, such as, for example, oxanilide, isophthalic acid dihydrazide, sebacic acid bis-phenylhydrazide, bis-benzylidene-oxalic acid dihydrazide, N,N'-diacetyl-adipic acid dihydrazide, N,N'-bis-salicyloyl-oxalic acid dihydrazide, N,N'-bis-salicyloyl-hydrazine, N,N'-bis-(3,5-di-tert.butyl-4-hydroxyphenylpropionyl)-hydrazine, N-salicylal-N'-salicylidenehydrazine and 3 salicyloylamino-1,2,4-triazole.

Thiosynergists can also be employed with the stabilizers of this invention. The thiosynergists can be represented by the formula

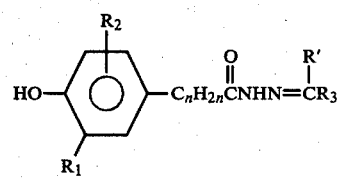

wherein R is an alkyl group having from 6 to 24 carbon atoms; and m is an integer from 1 to 6. Especially useful thiosynergists are dilauryl-β-thiodipropionate and distearyl-β-thiodiproprionate tetrakis[methylene-2-dodecylthiopropionate] methane dimyristylthiodipropionate.

What is claimed is:

1. A hindered phenol hydrazone of the formula

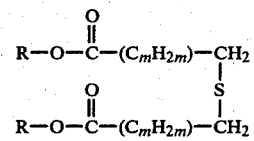

wherein
$R_1$ is hydrogen of a straight or branched chain alkyl of 1 to 8 carbon atoms,
$R_2$ a straight or branched chain alkyl of 1 to 8 carbon atoms,
n is an integer of 1 to 5,
$R^1$ is hydrogen or alkyl of 1 to 8 carbon atoms,
$R_3$ is an alkyl of 1 to 18 carbon atoms, phenyl or phenyl substituted with 1 to 3 alkyl groups of 1 to 4 carbon atoms, or selected from an interrupted alkyl group of the formulae

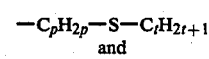

and

-continued

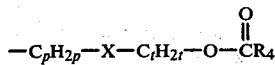

where p and t are independently integers of 1 to 18, $R_4$ is an alkyl group of 1 to 17 carbon atoms or an olefinic group of the formula $-(CH_2)_z-CH=CH(CH_2)_y CH_3$ where z and y are independently integers of 1 to 12, or $R_3$ is the group

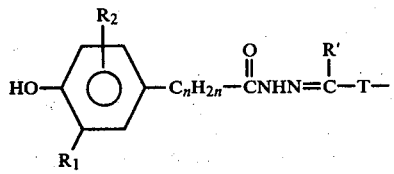

where T is a direct bond, alkylene of 1 to 6 carbon atoms, phenylene, alkylene interrupted with sulfur or oxygen of the formula $-(C_aH_{2a})-X-(C_aH_{2a})-$ where X is sulfur or oxygen and a is an integer of 1 to 6.

2. A compound of claim 1 wherein $R_1$ and $R_2$ are branched chain alkyl groups, both ortho to the hydroxy, n is 2, $R_3$ is an interrupted alkyl group where p is 2 to 6 and t is 8 to 18.

3. A compound of claim 2 wherein $R_1$ and $R_2$ are tert-butyl groups.

4. The compound of claim 1 which is n-dodecylthio-2-methylpropanal-3'-(3'',5''-di-t-butyl-4''-hydroxyphenyl) propionyl hydrazone.

5. The compound of claim 1 which is n-dodecylthiopropanal-3-(3',5'-t-butyl-4'-hydroxyphenyl) propionyl hydrazone.

6. The compound of claim 1 which is oleoylethylthio-2-methylpropanal-3'-(3'',5''-di-t-butyl-4''-hydroxyphenyl) propionyl hydrazone.

7. A compound of claim 1 wherein $R_1$ and $R_2$ are branched chain alkyl groups, both ortho to the hydroxy, n is 2 and $R_3$ is hydrogen, alkyl or phenyl.

8. A compound of claim 1 wherein $R_1$ and $R_2$ are tert-butyl groups.

9. The compound of claim 8 which is n-dodecylal-3-(3',5'-di-t-butyl-4'-hydroxyphenyl)propionyl hydrazone.

10. The compound of claim 8 which is isovaleral-3-(3',5'-di-t-butyl-4'-hydroxyphenyl)propionyl hydrazone.

11. A compound of claim 1 wherein $R_1$ and $R_2$ are branched chain alkyl groups, both ortho to the hydroxy, n is 2 and $R_3$ is a group of the formula

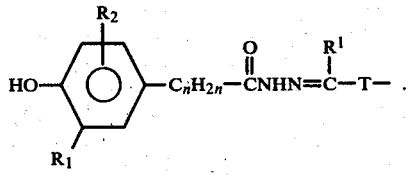

12. A compound of claim 11 wherein $R_1$ and $R_2$ are tert-butyl groups.

13. A polymer composition comprising a polymer selected from the group consisting of polymonoolefin resins and diene rubbers stabilized against thermal and oxidative degradation by incorporation therein of 0.01 to 5% by weight of a compound of claim 1.

14. A composition of claim 13 wherein said polymer is a rubber selected from polybutadiene, styrene-butadiene copolymer, acrylonitrile-butadiene-styrene copolymer and polyisoprene.

15. A composition of claim 14 wherein said rubber is polybutadiene.

16. A composition of claim 14 wherein the hydrazone stabilizer is 3-(3',5'-di-t-butyl-4'-hydroxyphenyl)propionyl (n-tridecylthio-2-methylpropanal)hydrazone.

* * * * *